(12) United States Patent
Li

(10) Patent No.: US 11,426,475 B2
(45) Date of Patent: Aug. 30, 2022

(54) UV STERILIZATION DEVICE FOR CONTAINER

(71) Applicant: Xiaohui Li, Shenzhen (CN)

(72) Inventor: Xiaohui Li, Shenzhen (CN)

( * ) Notice: Subject to any disclaimer, the term of this patent is extended or adjusted under 35 U.S.C. 154(b) by 518 days.

(21) Appl. No.: 16/538,799

(22) Filed: Aug. 12, 2019

(65) Prior Publication Data

US 2020/0289685 A1 Sep. 17, 2020

(30) Foreign Application Priority Data

Mar. 13, 2019 (CN) ......................... 20191018 8145.1

(51) Int. Cl.
*A61L 2/10* (2006.01)
*A61L 2/26* (2006.01)

(52) U.S. Cl.
CPC ...... *A61L 2/10* (2013.01); *A61L 2/26* (2013.01); *A61L 2202/23* (2013.01)

(58) Field of Classification Search
CPC ........... A61L 2/10; A61L 2/26; A61L 2202/23
See application file for complete search history.

(56) References Cited

U.S. PATENT DOCUMENTS

| 5,507,060 A * | 4/1996 | Quimpo | A47L 15/0068 |
| | | | 134/158 |
| 6,405,398 B1* | 6/2002 | Seidel | A46B 13/00 |
| | | | 15/59 |
| 2002/0047060 A1* | 4/2002 | Juriga | B26D 3/225 |
| | | | 241/282.1 |
| 2012/0121457 A1* | 5/2012 | Farren | A61L 2/10 |
| | | | 250/492.1 |

FOREIGN PATENT DOCUMENTS

CA 2696044 A1 * 2/2009 ............... A61L 9/14

* cited by examiner

*Primary Examiner* — Kevin Joyner
*Assistant Examiner* — Changru Chen

(57) ABSTRACT

A UV sterilization device for a container includes a housing, a base, a receiving room formed between the housing and the base, a transmission member symmetrically and rotatably mounted on the base and including a clamp for clamping the container, an extension rod symmetrically mounted on the base and inserting into the container to stretch out and draw back relative to the container along the axial direction of the extension member, a UV sterilization member mounted on the extension member to move with the extension member, and a driving member fixed with the base and including a motor therein. The motor is fixed with the transmission member and the extension member. The motor can drive the transmission member and the container to rotate, and drive the extension member to stretch out and draw back relative to the container along the axial direction of the extension member to further drive the UV sterilization member to disinfect the container.

17 Claims, 10 Drawing Sheets

UV STERILIZATION DEVICE FOR CONTAINER

BACKGROUND

1. Technical Field

The present disclosure generally relates to disinfection and sterilization devices field, and especially relates to a UV sterilization device for a container.

2. Description of Related Art

As we all known, with the development of society, people pay more and more attention to their health problems. In order to ensure food sanitation, all kinds of containers, such as milk bottles and cups, are often needed disinfection before using them. In general, conventional disinfection methods for such container above mentioned include a boil disinfection method and a steam pan disinfection method. However, such two disinfection methods have some disadvantages: the boil disinfection method not only takes time and energy, but also is complex to be operated and poor disinfection effect; while, the steam pan disinfection method is very inconvenient to be operated, and is easily to cause secondary pollution and burn users. In addition, the container disinfected by means of such two disinfection methods is needed auxiliary tools to remove after it is completed full disinfection, which is so inconvenient.

SUMMARY

The technical problems to be solved: in view of the shortcomings of the related art, the present disclosure relates to a UV sterilization device for a container which can not only have a good disinfection and bactericidal effect on the harmful bacteria, pathogenic bacteria and molds left on the container with a minimize disinfection time, but also achieve all-round sterilization by simple operation.

The technical solution adopted for solving technical problems of the present disclosure is:

a UV sterilization device for a container includes a housing, a base connected to the housing, and a receiving room formed between the housing and the base for receiving a pair of transmission members, a pair of extension members, a pair of UV sterilization members, a driving member and the container therein. The pair of transmission members is symmetrically mounted on the base to rotate relative to the base and includes a clamp for clamping the container. The pair of extension members is symmetrically mounted on the base and can pass through corresponding transmission members and then extend into the container so that the pair of extension members can stretch out and draw back relative to the container along an axial direction thereof. Each UV sterilization member is mounted on a corresponding extension member to move together with the corresponding extension member. The driving member is fixed with the base and includes a motor therein. The motor is fixed with both the pair of transmission members and the pair of extension members, and configured to not only drive the pair of transmission members to rotate and then drive the container to rotate, but also drive the pair of extension members to stretch out and draw back relative to the container along the axial direction of the extension member to further drive a corresponding UV sterilization member to sterilize the container.

Wherein the transmission member further includes a driven gear connected to the motor, and a connecting portion fixed with the clamp and the driven gear, and the motor is configured to drive the driven gear to rotate and then drive the container clamped by the clamp to rotate with the driven gear.

Wherein the hardness of the clamp is less than that of the container.

Wherein the clamp includes a first clamping portion with a cone inner torus thereon, a second clamping portion coaxially arranged with the first clamping portion and an annular groove surrounded between the first clamping portion and the second clamping portion for receiving an opening of the container therein, and the diameter of the first clamping portion is greater than that of the second clamping portion.

Wherein the UV sterilization device further includes a rotating member received in the receiving room and including a rotating gear fixed with the motor and engaged with the driven gear, and a winding member which includes a single-groove tightly fixed with the rotating gear and a connecting member, two opposite ends of the connecting member respectively connected to the pair of extension members for pulling the pair of extension members to stretch out and draw back along the axial direction of the extension member relative to the container, the motor configured to drive the rotating gear and the single-groove pulley to rotate so as to respectively drive the driven gear to rotate and the pair of extension members to coaxially stretch out and draw back.

Wherein the single-groove pulley includes an inner disk body, a connecting post fixed with the rotating gear, and an outer disk body with a clamping slot extending along its radial direction from the outer disk body to an inner end surface of the inner disk body, the connecting member laterally passing through the clamping slot, all the inner disk body, the connecting post and the outer disk body coaxially arranged with the rotating gear, and the diameter of the outer disk body same as the diameter of the inner disk body, but greater than that of the connecting post.

Wherein the base includes a body, an upper plate mounted on the upper end of the body, and a baseboard mounted on the bottom end of the body, the upper plate including a pair of through-holes for the pair of transmission members correspondingly passing therethrough and a receiving recess with its opening facing downward for receiving the motor therein.

Wherein the base further includes an installing frame including a first fixing frame fixed with the upper plate, and a second fixing frame fixed with the first fixing frame.

Wherein the first fixing frame includes an installing hole connected with the through-hole, an installing portion and a hole, the transmission member passing through the through-hole to rotatably mount on the installing hole, and the motor includes a motor body received in the receiving recess and mounted on the installing portion, and a motor shaft passing through the hole and fixed with the rotating gear.

Wherein the second fixing frame includes a fixing post passing through the installing hole and the through-hole, and a locating hole for the single-groove pulley passing therethrough, the pair of extension members respectively received in corresponding fixing posts so as to stretch out and draw back from the corresponding fixing post.

Wherein the UV sterilization device further includes a pulley assembly received in the receiving room and including a pulley frame fixed with the bottom of the fixing post, and a pair of pulleys rotatably mounted on the pulley frame, one of the two opposite ends of the connecting member fixed with one of the pair of extension members, the other of the two opposite ends of the connecting member passing through one of the pair of pulleys, the clamping slot and the other of the pair of pulleys in turn, and then fixed with the other of the pair of extension members.

Wherein the extension member includes a first extension rod received in the fixing post and configured to stretch out and draw back from the fixing post, a second extension rod and a resetting member respectively connected to the first extension rod, the second extension rod received in the first extension rod and configured to stretch out and draw back from the first extension rod, one portion of the resetting member fixed with the second extension rod and the opposite portion passing through both the first extension rod and the fixing post and then resisted against the pulley frame.

Wherein the first and second extension rods and the fixing post are cooperatively connected to form a passageway for receiving the resetting member therein, and the connecting member is partially received in the passageway.

Wherein the first extension rod includes a first hollow post including a pair of first L-shaped ribs coaxially arranged on its outer wall thereof, and a first ring protruding outward from its lower portion thereof and including a first gap formed thereon; the fixing post including a second barrier formed on its inner wall thereof, and a second blocking torus connected to the upper portion of the second barrier and including a second notch formed thereon; the second barrier passing through the first gap and the first L-shaped rib to slide in the second notch; and wherein the first ring is resisted against the second blocking torus when the first L-shaped rib slides to the top of the fixing post.

Wherein the first post includes a first barrier formed on its inner sidewall thereof, and a first blocking torus connected to the upper end of the first barrier and including a first notch formed thereon; the second extension rod including a second hollow post including a pair of second L-shaped ribs coaxially arranged on its outer sidewall thereof, and a second ring protruding outward from its lower end thereof and including a second gap formed thereon; the first barrier passing through both the second gap and the second L-shaped rib to slide in the first notch; and wherein the second ring is resisted against the first blocking torus when the second L-shaped rib slides to the top of the first extension rod.

Wherein the second post further includes a V-shaped strip, the two opposite ends of the connecting member fixed with the V-shaped strip, respectively, and the other portion of the resetting member also resisted against the V-shaped strip.

Wherein an inserting hook is connected with the second post for elastically clamping the UV sterilization member to tightly fix the second extension rod with the UV sterilization member.

Wherein the UV sterilization member includes a heat sink elastically clamped on the inserting hook, a lateral LED fixed with the outer side of the heat sink, an end LED fixed with the top portion of the heat sink, and a pressing buckle clamping the end LED and fixed with the heat sink.

Wherein the heat sink includes a first mounting slot for receiving the lateral LED therein, and a second mounting slot for receiving the end LED therein.

Wherein the heat sink further includes a sliding recess, a buckle and a rail formed between the sliding recess and the buckle, and the inserting hook includes a base portion received in the sliding recess, and a hooking portion received in the buckle and snapped with the rail.

The present disclosure provides the advantages as below.

The UV sterilization device of the present disclosure can not only have a good disinfection and bactericidal effect on the harmful bacteria, pathogenic bacteria and molds left on the container with a minimize disinfection time, but also achieve all-round sterilization by means of the clamp clamping the container, the transmission member driving the container to rotate, and the extension member simultaneously driving the UV sterilization member to stretch out and draw back relative to the container along the axial direction of the extension member.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

Figure 1:
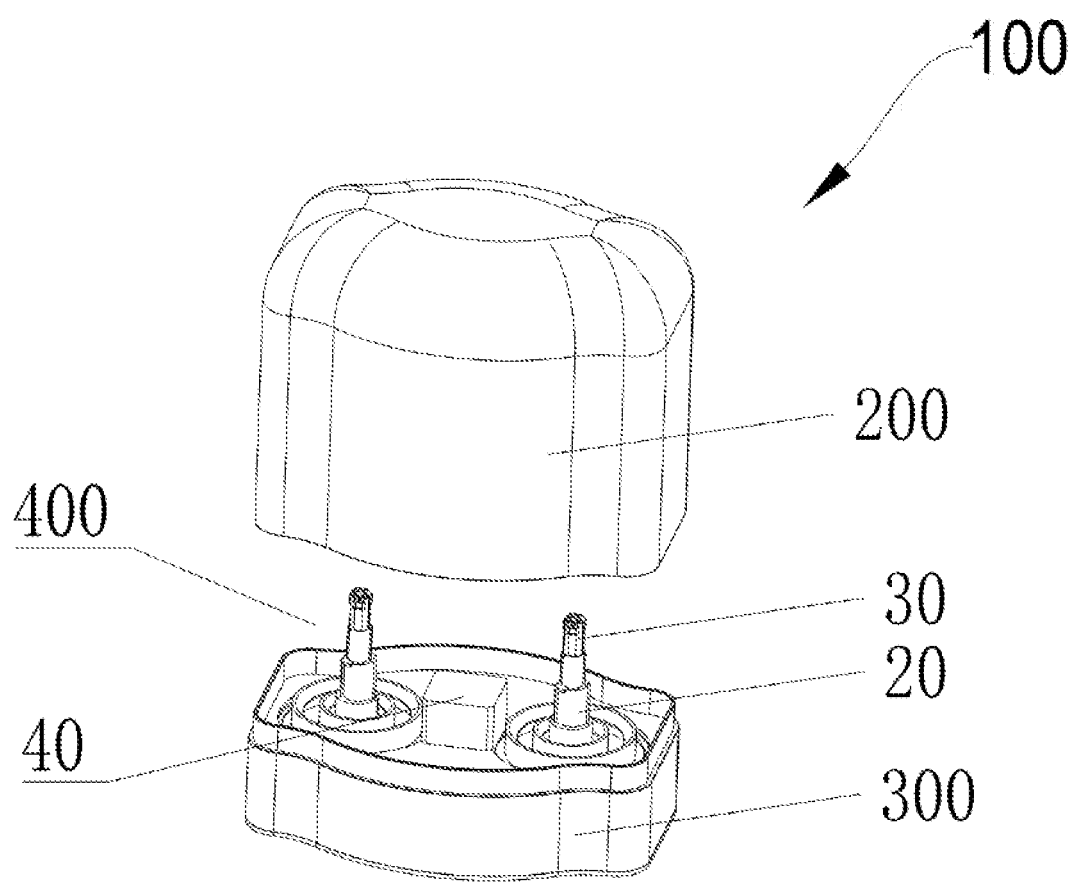
FIG. 1 is an exploded, schematic view of the UV sterilization device for a container in accordance with an exemplary embodiment.

The element labels according to the exemplary embodiment of the present disclosure shown as below:

UV sterilization device 100, housing 200, base 300, upper plate 301, through-hole 3011, body 302, upper end 302a, bottom end 302b, baseboard 303, installing frame 304, first fixing frame 3041, second fixing frame 3042, installing hole 3043, installing portion 3044, hole 3045, fixing post 3046, bottom 3046a, inner wall 3041a, locating hole 3047, second barrier 3048, upper portion 3048a, second blocking torus 3049, second notch 3050, receiving room 400, transmission member 10, clamp 11, first clamping portion 111, inner torus 11a, annular groove 112, second clamping portion 113, connecting portion 12, driven gear 13, extension member 20, first extension rod 21, first post 211, outer wall 211a, lower portion 211b, inner sidewall 211c, first barrier 2111, upper end 2111a, first blocking torus 2112, first notch 2113, first L-shaped rib 212, first ring 213, first gap 2131, second extension rod 22, second post 221, outer sidewall 221a, lower end 221b, V-shaped strip 2211, second L-shaped rib 222, second ring 223, second gap 2231, resetting member 23, one portion 23a, the other portion 23b, passageway 24, inserting hook 224, base portion 2241, hooking portion 2242, UV sterilization member 30, heat sink 31, outer side 31a, top portion 31b, first mounting slot 311, second mounting slot 312, sliding recess 313, buckle 314, rail 315, lateral LED 32, end LED 33, pressing buckle 34, window 341, driving member 40, motor 41, motor body 411, motor shaft 412, rotating member 50, rotating gear 51, winding member 52, single-groove pulley 521, inner disk body 5211, inner end surface 5211a, connecting post 5212, outer disk body 5213, clamping slot 5214, pulley assembly 60, pulley frame 61, pulley 62, connecting member 63, opposite ends 63a, container 500, opening 501.

DETAILED DESCRIPTION

The disclosure is illustrated by way of example and not by way of limitation in the figures of the accompanying drawings, in which like reference numerals indicate similar elements.

In the description of the present disclosure, it needs to be understood that the terms mentioned below: "central", "longitudinal", "transverse", "length", "width", "thickness", "upper", "below", "front", "back", "left", "right", "vertical", "horizontal", "top", "bottom", "inner", "outer", "clockwise", "anticlockwise", etc, are shown in the specification of the present disclosure. The indicated orientation or position of the terms shown in the detailed description is based on the orientation or position shown in the figures of the accompanying drawings of the present disclosure, which is only to easily simplify the description of the present disclosure, but not indicated that the devices or elements of the present disclosure should have a particular orientation or should be designed and operated in a particular orientation. So the terms illustrated in the detail description are not by way of the limitation of the present disclosure.

In addition, the terms such as "first" and "second" shown in the specification are only used to describe, but not indicated that the elements of the present disclosure is important or represented the amount of the elements. That is, the features limited by the terms of "first" and "second" may explicitly or implicitly include one or more features. In the description of the present disclosure, the meaning of the term "a plurality of" is not less than two unless it is specifically illustrated.

In the present disclosure, except where specifically otherwise illustrated or limited, the terms "install", "connect", "link" and "fix" used herein should be understood in a broad sense. Such as, the meaning may be tight connection, removable connection, or integrated connection. The meaning may also be mechanical connection, electrical connection, direct connection or indirect connection through intermediaries, or internal connection within two elements. The meaning of the terms used herein may be understood by one of ordinary skill in the related art according to specific conditions of the present disclosure.

Referring to FIGS. 1-19, a UV sterilization device 100 for a container 500 in accordance with an exemplary embodiment is provided. The UV sterilization device 100 includes a housing 200, a base 300 connected to the housing 200, and a receiving room 400 formed between the housing 200 and the base 300. The receiving room 400 is provided for receiving a pair of transmission members 10, a pair of extension members 20, a pair of UV sterilization members 30, a driving member 40 and the container 500 therein.

The pair of transmission members 10 is symmetrically mounted on the base 300 to rotate relative to the base 300 and includes a clamp 11 for clamping the container 500.

The pair of extension members 20 is symmetrically mounted on the base 300 and passes through corresponding transmission members 10 and then extends into the container 500 so that the pair of extension members 20 can stretch out and draw back relative to the container 500 along an axial direction thereof.

Each UV sterilization member 30 is mounted on a corresponding extension member 20 to move together with the corresponding extension member 20.

The driving member 40 is fixed with the base 300 and includes a motor 41 therein.

The motor 41 is fixed with both the pair of transmission members 10 and the pair of extension members 20, and configured to not only drive the pair of transmission members 10 to rotate and then drive the container 500 to rotate, but also drive the pair of extension members 20 to stretch out and draw back relative to the container 500 along the axial direction of the extension member 20 to further drive a corresponding UV sterilization member 30 to sterilize the container 500.

The UV sterilization device 100 of the present disclosure is provided that the UV sterilization member 30 can not only have a good disinfection and bactericidal effect on the harmful bacteria, pathogenic bacteria and molds left on the container 500 with a minimize disinfection time, but also achieve all-round sterilization by the clamp 11 clamping the container 500, the transmission member 10 driving the container 500 to rotate, and the extension member 20 simultaneously driving the UV sterilization member 30 to stretch out and draw back relative to the container 500 along the axial direction of the extension member 20.

In usage, the container 500 is clamped by the clamp 11, the pair of transmission members 10 is driven by the motor 41 to rotate and then the container 500 is following rotating with the transmission member 10. At the same time, The motor 41 is also configured to drive the pair of extension members 20 to stretch out and draw back relative to the container 500 along the axial direction of the extension member 20 to further drive a corresponding UV sterilization member 30 to all-round sterilize the container 500.

In an exemplary embodiment of the present disclosure, light emitted from the UV sterilization member 30 includes ultraviolet light at the wavelength of 150~300 nm UVC band and blue light at the wavelength of 400~470 nm. The ultraviolet light of UVC band is mainly played as the role of sterilization, thereby such ultraviolet light in this wavelength range has excellent killing effect on most bacteria and pathogenic bacteria found so far. Therefore, it has a good antibacterial and antitoxic effect on the harmful bacteria, pathogenic bacteria and molds left on the container 500. In addition, the blue light is mainly played as the role of anti-mold so that it is usually used to remove molds, thereby an excellent disinfection and anti-mold effect by simple operation can be achieved.

In an exemplary embodiment of the present disclosure, the sterilization device 100 is mainly used for disinfecting milk bottles. Of course, the UV sterilization device 100 can also be used to disinfect other containers, such as drinking water bottles. When the sterilization device 100 of the present disclosure is applied to disinfect the milk bottle, the caliber of the clamp 11 is provided with two specifications of a wide-mouth and a standard-mouth. Furthermore, the standard-mouth is a uniform diameter of the milk bottle stipulated by our country so that the UV sterilization device 100 of the present disclosure can be used for disinfecting various milk bottles, thereby the applicability of the UV sterilization device 100 is improved. In addition, the UV sterilization device 100 can simultaneously disinfect various containers 500 with a minimize disinfection time.

Furthermore, referring to FIG. 1, FIG. 2, FIG. 5 and FIG. 8, the transmission member 10 further includes a driven gear 13 connected to the motor 41, and a connecting portion 12 fixed with the clamp 11 and the driven gear 13. The motor 41 is configured to drive the driven gear 13 to rotate and then drive the container 500 clamped by the clamp 11 to rotate with the driven gear 13.

In an exemplary embodiment of the present disclosure, the clamp 11 is fixed with connecting portion 12 and the driven gear 13 via a clamping way so that the clamp 11 can be disassembled and cleaned conveniently, and can be also very simple and convenient to install again.

Preferably, the hardness of the clamp 11 is less than that of the container 500. In an exemplary embodiment of the present disclosure, the clamp 11 is made of silica gel, with safe and non-toxic, good tear resistance and resilience, so that it can be clamped on an opening 501 of the container 500, and easily and quickly removed from the transmission member 10.

Furthermore, the clamp 11 includes a first clamping portion 111, a second clamping portion 113 coaxially arranged with the first clamping portion 111 and an annular groove 112 surrounded between the first clamping portion 111 and the second clamping portion 113 for receiving the opening 501 of the container 500 therein. The first clamping portion 111 includes a cone inner torus 111a formed thereon to increase the extrusion pressure of the first clamping portion 111 applied on the opening 501 of the container 500 to further stably clamp the container 500. In an exemplary embodiment of the present disclosure, the diameter of the first clamping portion 111 is greater than that of the second clamping portion 113.

Referring to FIGS. 1-3 and FIG. 14, the UV sterilization device 100 further includes a rotating member 50 received in the receiving room 400. The rotating member 50 includes a rotating gear 51 fixed with the motor 41 and engaged with the driven gear 13, and a winding member 52 which includes a single-groove pulley 521 fixed with the rotating gear 51 and a connecting member 63. Two opposite ends 63a of the connecting member 63 are respectively connected to the pair of extension members 20 for pulling the pair of extension members 20 to stretch out and draw back along the axial direction of the extension member 20 relative to the container 500. The motor 41 is configured to drive the rotating gear 51 and the single-groove pulley 521 to rotate so as to respectively drive the driven gear 13 to rotate and the pair of extension members 20 to coaxially stretch out and draw back.

In an exemplary embodiment of the present disclosure, the connecting member 63 is a wire rope with good softness, high tensile strength, high fatigue strength and good impact toughness so that it is suitable for traction and pulling. Moreover, the self-weight of the wire rope is light, thereby the volume and weight of the UV sterilization device 100 of the present disclosure can be minimized. Of course, such functions mentioned above can be obtained by other ways.

Figure 16:
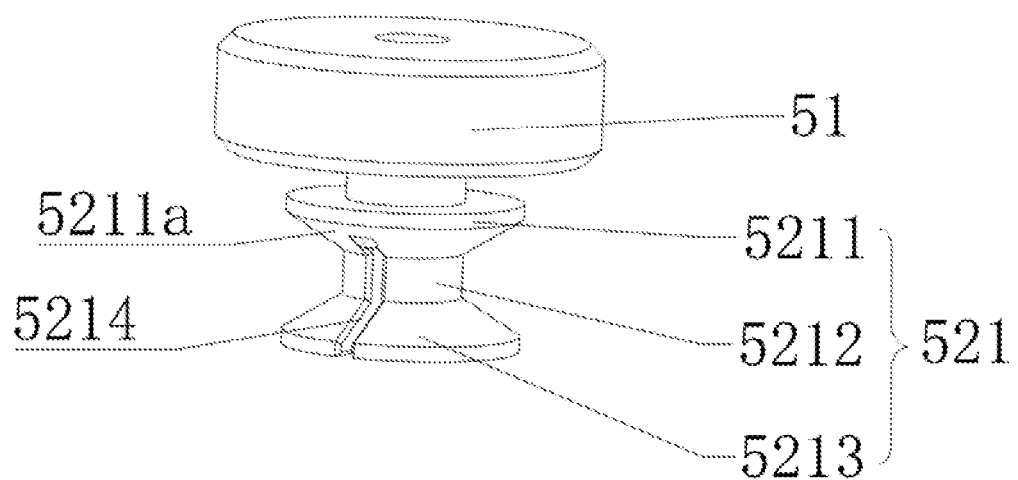
FIG. 16 is a schematic view of the rotating member of the UV sterilization device of FIG. 14.
Figure 17:
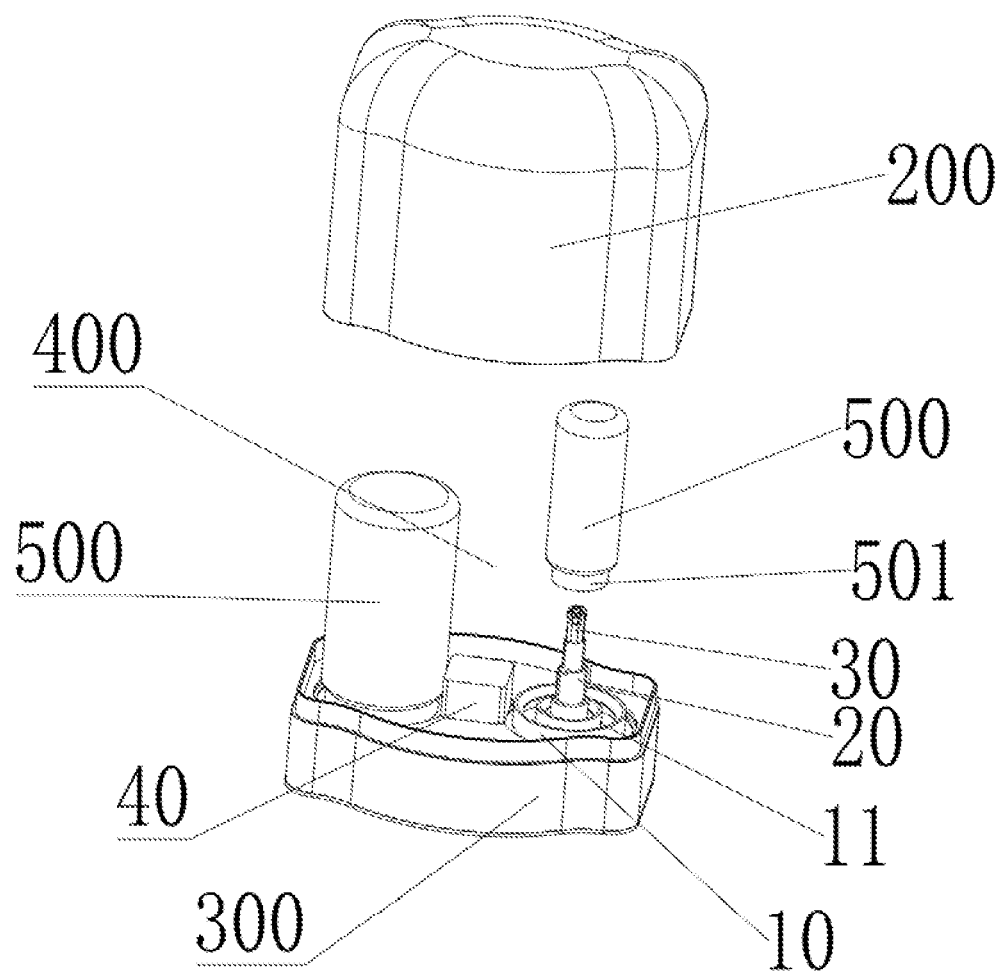
FIG. 17 is a schematic view of the UV sterilization device and the container of FIG. 1, shown in a usage state.

Furthermore, referring to FIG. 16, the single-groove pulley 521 includes an inner disk body 5211, a connecting post 5212 fixed with the rotating gear 51, and an outer disk body 5213 with a clamping slot 5214 extending along its radial direction from the outer disk body 5213 to an inner end surface 5211a of the inner disk body 5211. The connecting member 63 laterally passes through the clamping slot 5214. In an exemplary embodiment of the present disclosure, all the inner disk body 5211, the connecting post 5212 and the outer disk body 5213 are coaxially arranged with the rotating gear 51, and the diameter of the outer disk body 5213 is same as the diameter of the inner disk body 5211, but greater than that of the connecting post 5212.

In an exemplary embodiment of the present disclosure, the motor 41 is driven to rotate along a first direction so that the rotating gear 51 and the single-groove pulley 521 are also driven to rotate along the first direction. And then, the driven gear 13 is also rotated to drive the container 500 to rotate with the rotating gear 51. At the same time, the connecting member 63 is wound on the single-groove pulley 521 along the first direction so that the pair of extension members 20 is compressed by pulling of the connecting member 63. When the pair of extension members 20 is compressed to its lowest compression position, the motor 41 is driven to rotate along a second direction, the pair of extension members 20 is stretched out along the second direction so as to achieve all-round sterilization of the container 500. It can be understood that the first direction is opposite to the second direction, such as the first direction is clockwise, while the second direction is counterclockwise.

Figure 10:
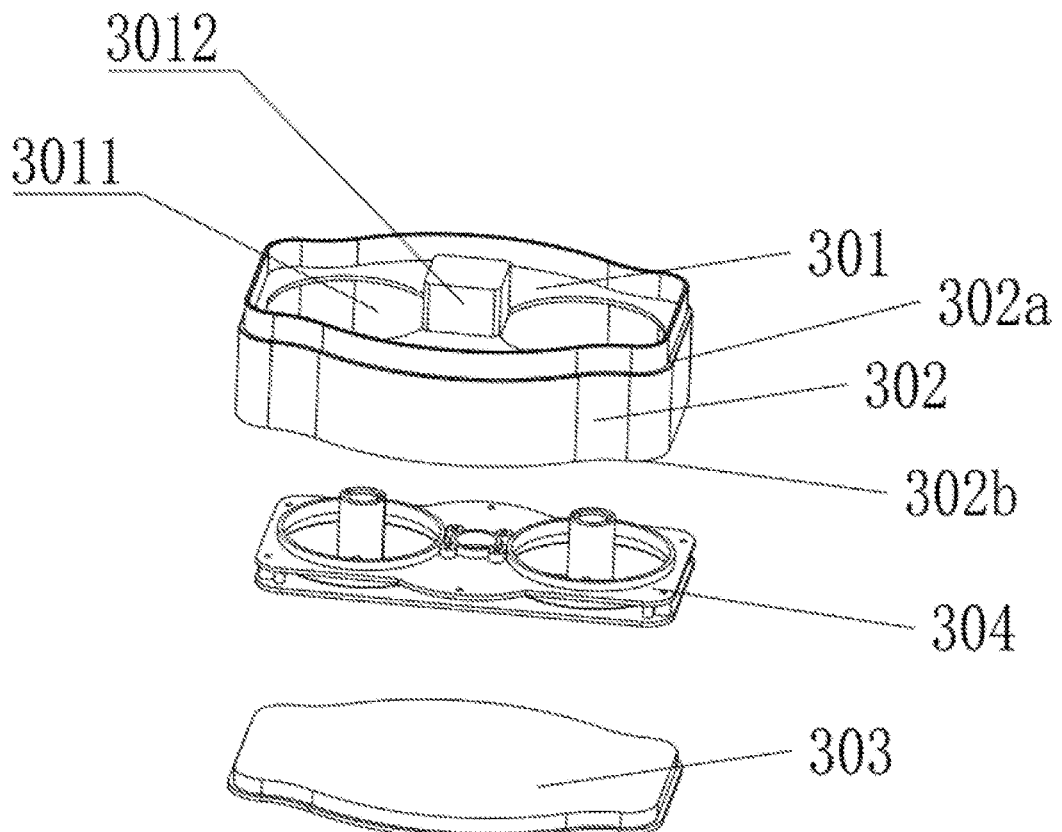
FIG. 10 is a schematic view of a base of the UV sterilization device of FIG. 1.
Figure 11:
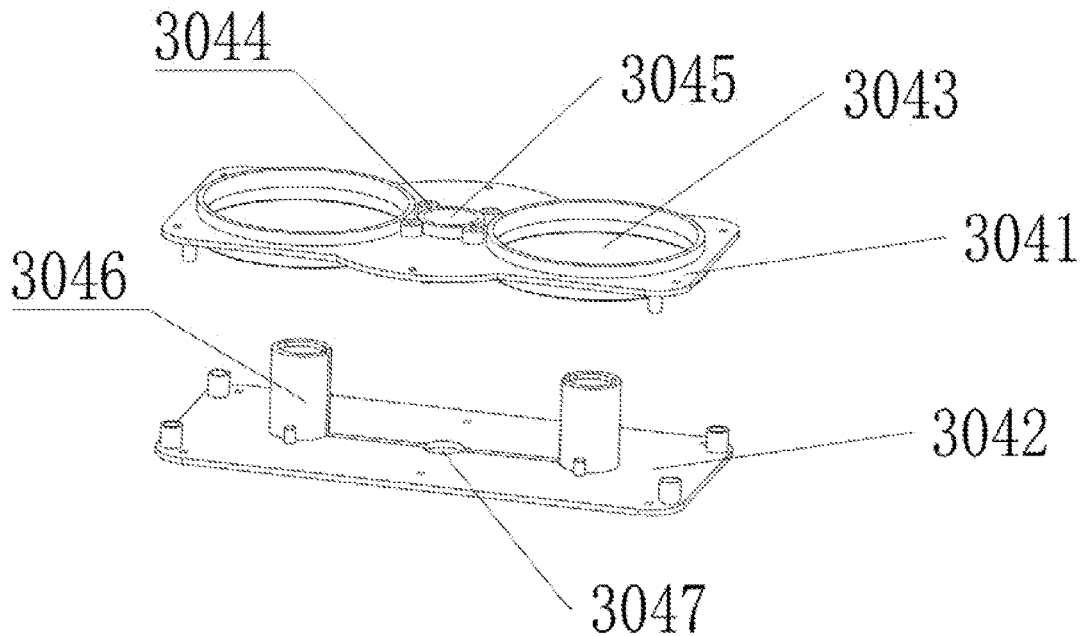
FIG. 11 is a schematic view of an installing frame of the UV sterilization device of FIG. 1.

Referring to FIG. 1, FIG. 10 and FIG. 11, the base 300 includes a body 302, an upper plate 301 mounted on the upper end 302a of the body 302, and a baseboard 303 mounted on the bottom end 302b of the body 302. The upper plate 301 includes a pair of through-holes 3011 corresponding to the pair of transmission members 10 and a receiving recess 3012 with its opening facing downward for receiving the motor 41 therein. The pair of transmission members 10 can pass through the pair of through-holes 3011, correspondingly.

Preferably, the base 300 further includes an installing frame 304 which includes a first fixing frame 3041 fixed with the upper plate 301, and a second fixing frame 3042 fixed with the first fixing frame 3041.

Figure 14:
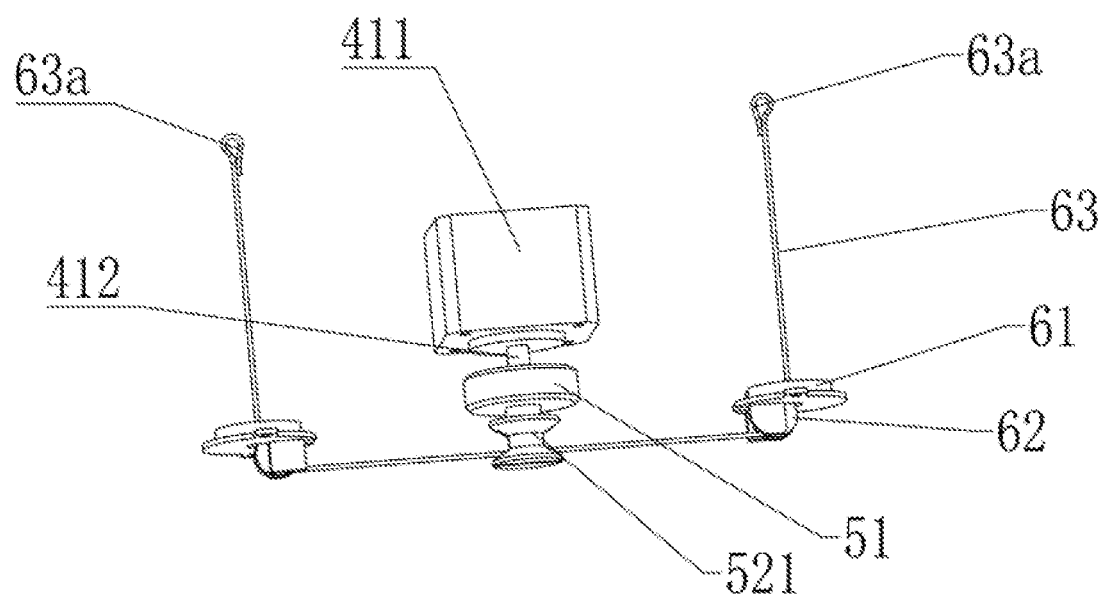
FIG. 14 is an assembly schematic view of a pulley assembly, a motor and a rotating member of the UV sterilization device of FIG. 1.
Figure 15:
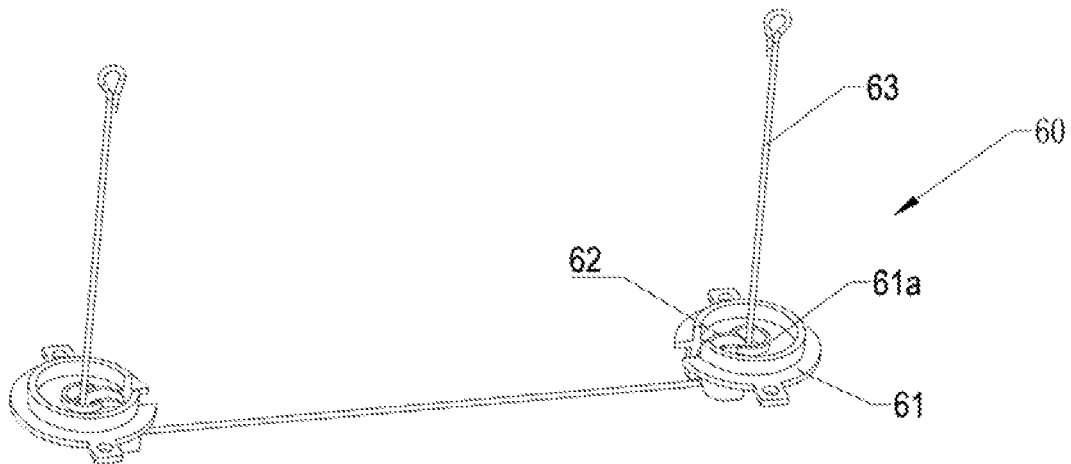
FIG. 15 is an assembly schematic view of the pulley assembly and a connecting member of the UV sterilization device of FIG. 1.

Referring to FIG. 11 and FIG. 14, the first fixing frame 3041 includes an installing hole 3043 connected with the through-hole 3011, an installing portion 3044 and a hole 3045. The pair of transmission members 10 passes through the corresponding through-holes 3011 to rotatably mount on the installing hole 3043, and the motor 41 includes a motor body 411 received in the receiving recess 3012 and downwardly mounted on the installing portion 3044, and a motor shaft 412 passing through the hole 3045 and fixed with rotating gear 51.

Referring to FIG. 11, the second fixing frame 3042 includes a fixing post 3046 passing through the installing hole 3043 and the through-hole 3011, and a locating hole 3047 for the single-groove pulley 521 passing therethrough. The pair of extension members 20 is respectively received in corresponding fixing posts 3046 so as to stretch out and draw back from the fixing post 3046.

Figure 2:
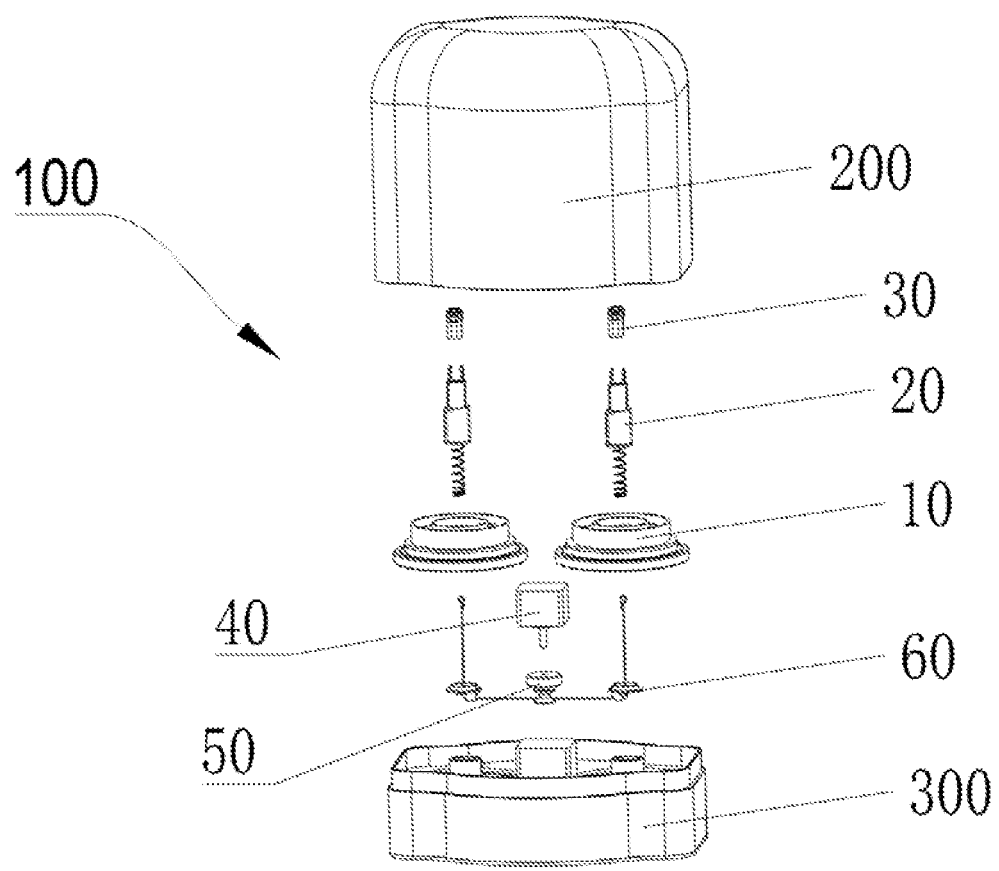
FIG. 2 is an exploded view of the UV sterilization device of FIG. 1.
Figure 3:
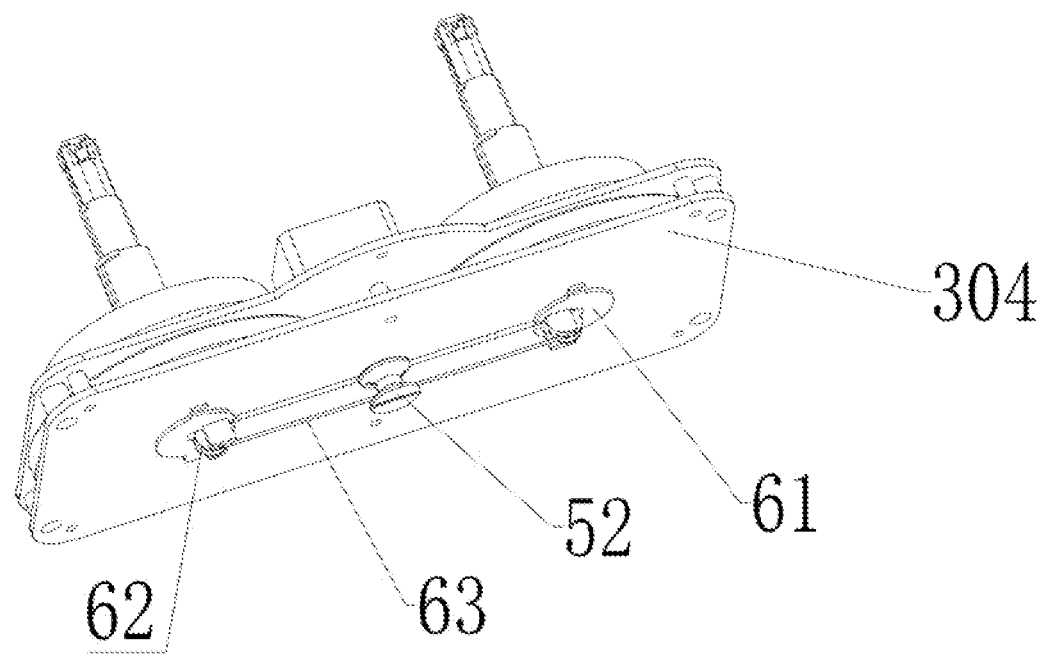
FIG. 3 is a partial schematic view of the UV sterilization device of FIG. 1.
Figure 4:
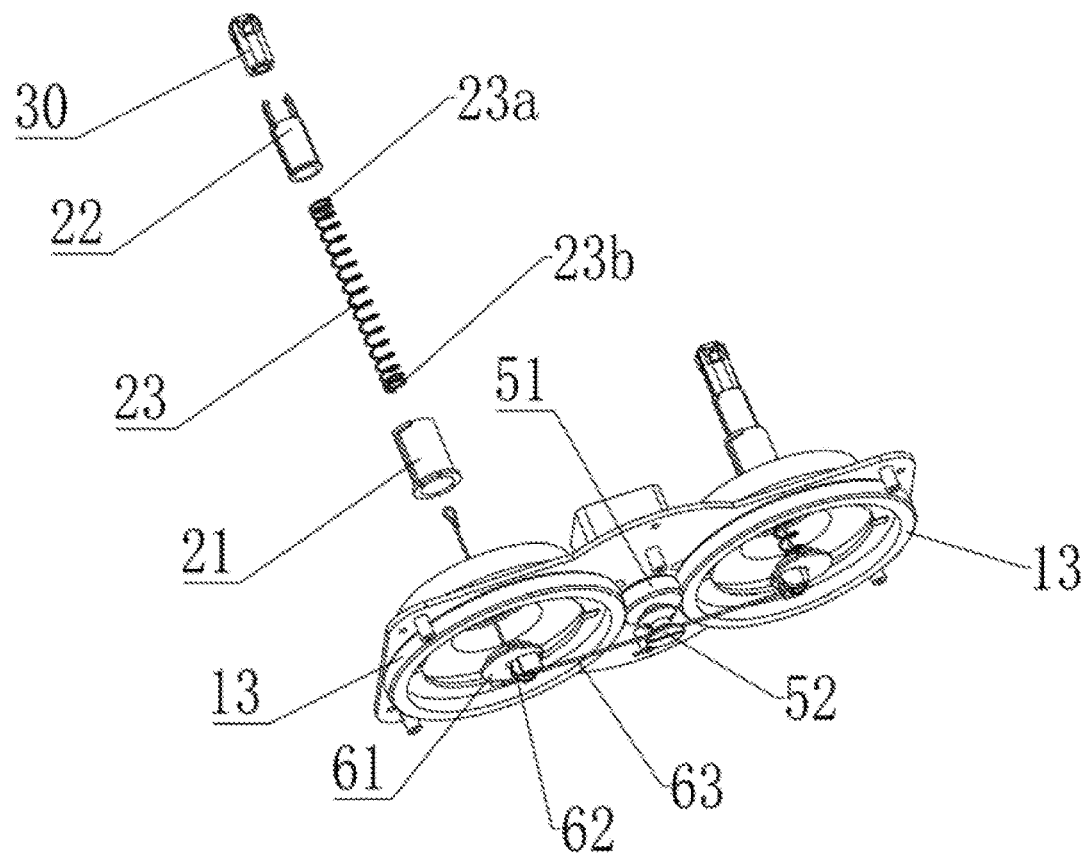
FIG. 4 is similar to FIG. 3, but shown an exploded state of FIG. 3.
Figure 5:
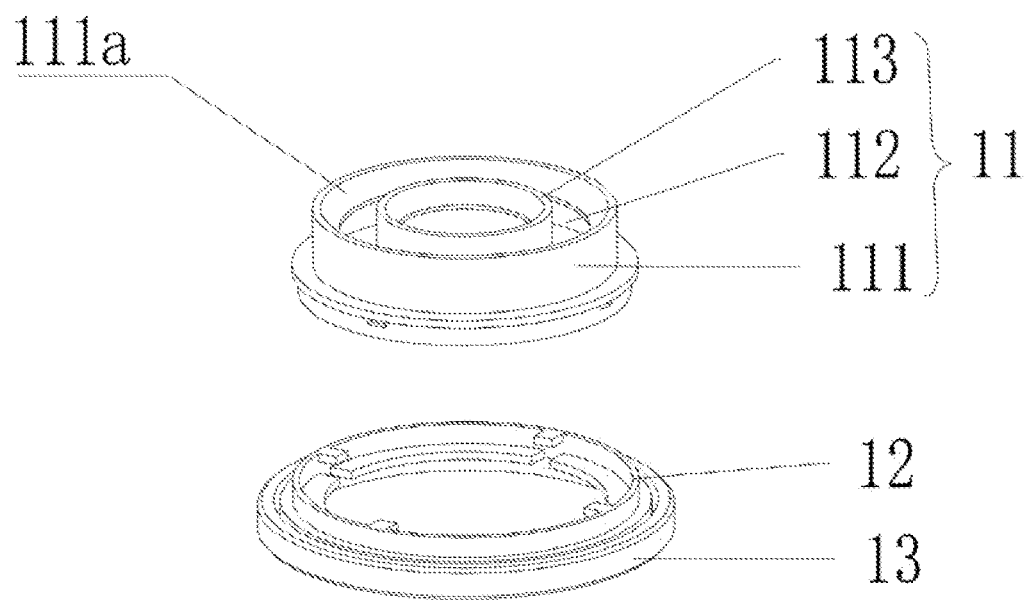
FIG. 5 is a schematic view of a transmission member of the UV sterilization device of FIG. 1.
Figure 19:
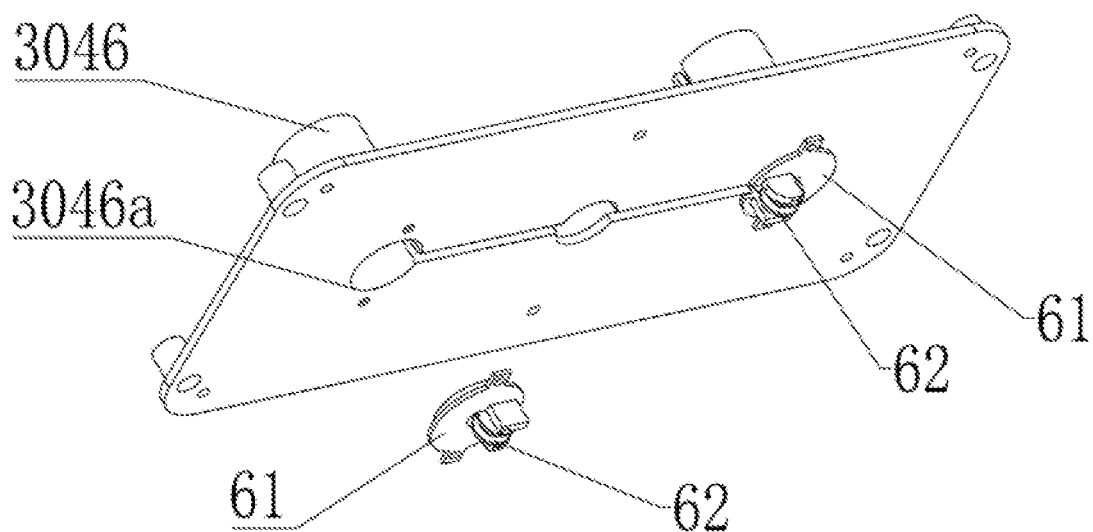
FIG. 19 is an assembly schematic view of the pulley assembly and a fixing post of the UV sterilization device of FIG. 1.

Furthermore, referring to FIG. 2, FIG. 3 and FIG. 19, the UV sterilization device 100 further includes a pulley assembly 60 received in the receiving room 400. The pulley assembly 60 includes a pulley frame 61 fixed with the bottom 3046a of the fixing post 3046, and a pair of pulleys 62 rotatably mounted on the pulley frame 61. One of the two opposite ends 63a of the connecting member 63 is fixed with one of the pair of extension members 20, the other of the two opposite ends 63a of the connecting member 63 passes through one of the pair of pulleys 62, the clamping slot 5214 and the other of the pair of pulleys 62 in turn, and then fixed with the other of the pair of extension members 20. The pulley assembly 60 is provided that the connecting member 63 can pull the pair of extension members 20 to stretch out and draw back along the axial direction of the extension member 20, thereby the clutter of the whole UV sterilization device 100 can be avoided to further improve stable operation of the UV sterilization device 100.

Figure 6:
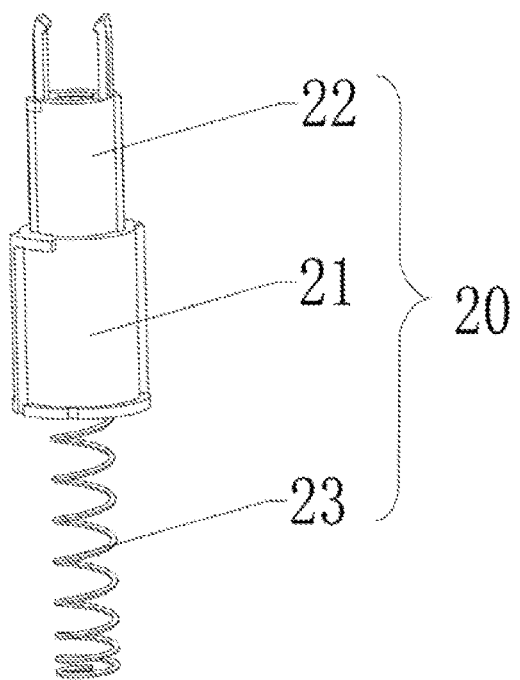
FIG. 6 is a schematic view of an extension member of the UV sterilization device of FIG. 1.

Referring to FIG. 6, the extension member 20 includes a first extension rod 21 received in the fixing post 3046 and configured to stretch out and draw back from the fixing post 3046, a second extension rod 22 and a resetting member 23 respectively connected to the first extension rod 21. The second extension rod 22 is received in the first extension rod 21 and configured to stretch out and draw back from the first extension rod 21. One portion 23a of the resetting member 23 is fixed with the second extension rod 22 and the opposite portion 23b of the resetting member 23 passes through the first extension rod 21 and the fixing post 3046 and then resists against the pulley frame 61.

In an exemplary embodiment of the present disclosure, the resetting member 23 is a spring so that both the first extension rod 21 and the second extension rod 22 can be reset under elasticity of the spring. In addition, the first extension rod 21 is connected with the second extension rod 22 so that the highest stretchable position of the extension member 20 can reach the bottom of the container 500, and the lowest compression position of the extension member 20 can also reach the opening 501 of the container 500, thereby achieving all-round sterilization without any dead angle to the container 500.

Figure 18:
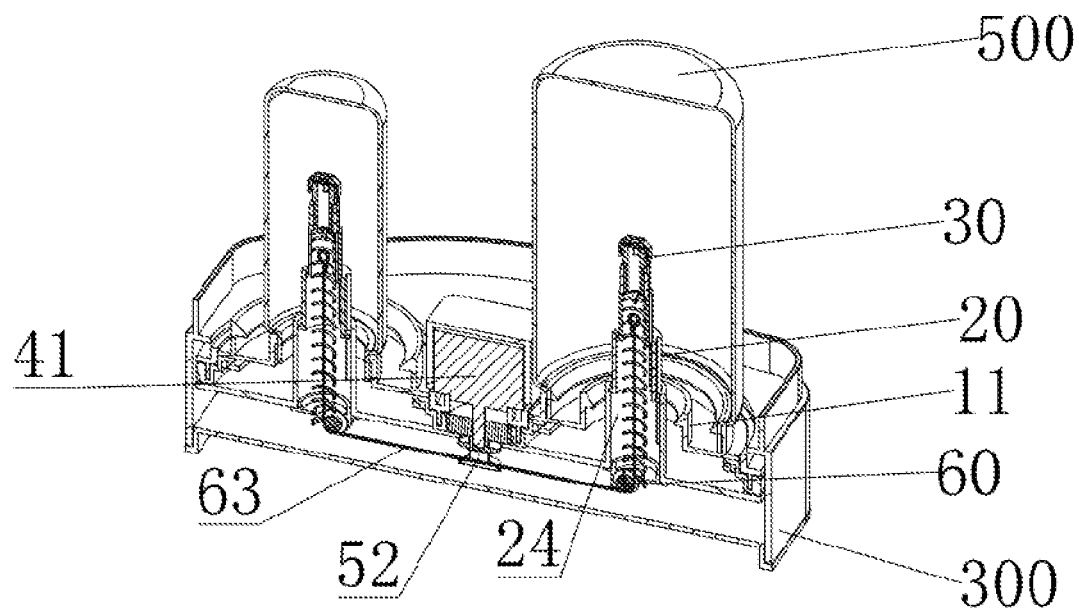
FIG. 18 is a cross-sectional schematic view of the UV sterilization device of FIG. 17, together with the container.

Preferably, referring to FIG. 18, the first extension rod 21 and the second extension rod 22 and the fixing post 3046 are cooperatively connected to form a passageway 24 to ensure smooth operation of the extension member 20. The resetting member 23 is received in the passageway 24, and the connecting member 63 is partially received in the passageway 24.

Figure 7:
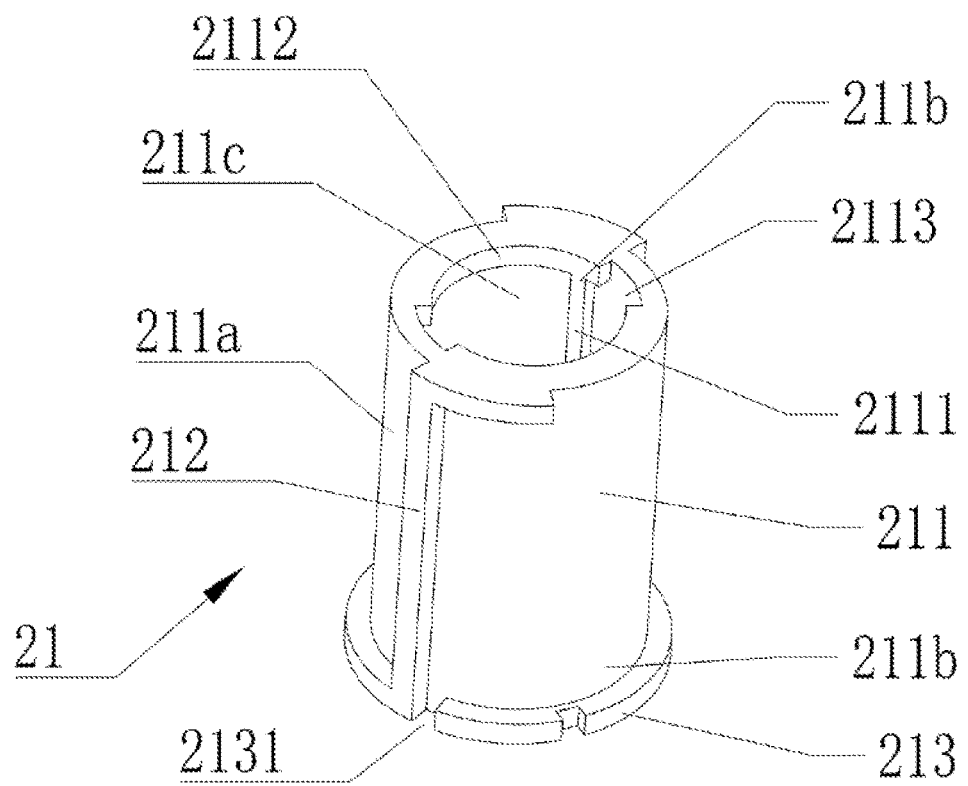
FIG. 7 is a schematic view of a first extension rod of the extension member of the UV sterilization device of FIG. 1.
Figure 9:
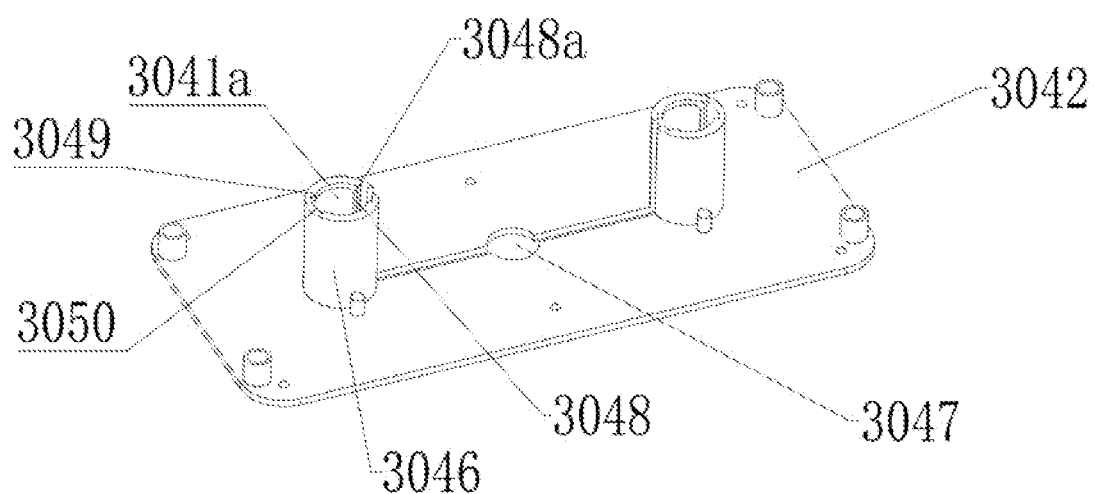
FIG. 9 is a schematic view of a second fixing frame of the UV sterilization device of FIG. 1.

Referring to FIG. 7 and FIG. 9, the first extension rod 21 includes a first hollow post 211 which includes a pair of first L-shaped ribs 212 coaxially arranged on its outer wall 211a thereof, and a first ring 213 protruding outward from its lower portion 211b thereof. The first ring 231 includes a first gap 2131 formed thereon.

The fixing post 6046 includes a second barrier 3048 formed on its inner wall 3041a thereof, and a second blocking torus 3049 connected to the upper portion 3048a of the second barrier 3048. The second blocking torus 3049 includes a second notch 3050 formed thereon.

The second barrier 3048 can pass through the first gap 2131 and the first L-shaped rib 212 can slide in the second notch 3050 to guide the movement of the first extension rod 21 in the fixing post 3046. The first ring 213 is resisted against the second blocking torus 3049 when the first L-shaped rib 212 slides to the top of the fixing post 3046 to prevent the first extension rod 21 from falling off the fixing post 3046.

Figure 8:
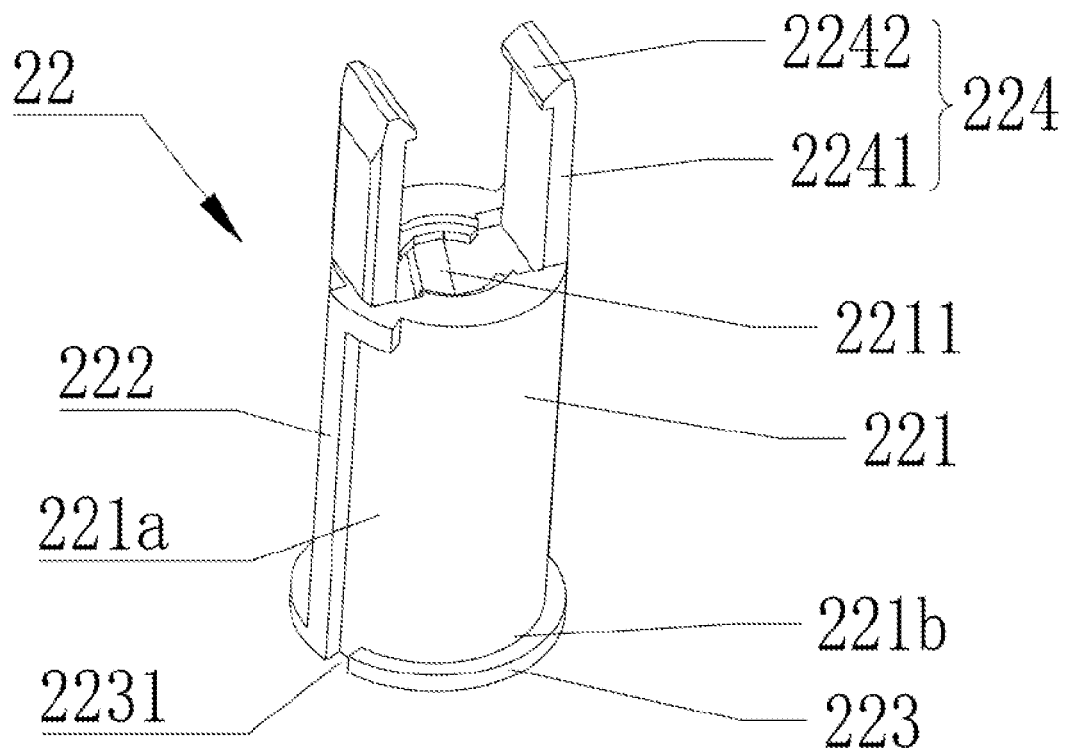
FIG. 8 is a schematic view of a second extension rod of the extension member of the UV sterilization device of FIG. 1.

Referring to FIG. 7 and FIG. 8, the first post 211 includes a first barrier 2111 formed on its inner sidewall 211c thereof, and a first blocking torus 2112 connected to the upper end 211a of the first barrier 2111. The first blocking torus 2112 includes a first notch 2113 formed thereon.

The second extension rod 22 includes a second hollow post 211 which includes a pair of second L-shaped ribs 222 coaxially arranged on its outer sidewall 221a thereof, and a second ring 223 protruding outward from its lower end 221b thereof. The second ring 223 includes a second gap 2231 formed thereon.

The first barrier 2111 can pass through the second gap 2231 and the second L-shaped rib 222 can slide in the first notch 2113 to guide the movement of the second extension rod 22 in the first extension rod 21. The second ring 223 is resisted against the first blocking torus 2112 when the second L-shaped rib 222 slides to the top of the first extension rod 21 to prevent the second extension rod 22 from falling off the first extension rod 21.

In an exemplary embodiment of the present disclosure, the second post 221 further includes a V-shaped strip 2211. The two opposite ends 63a of the connecting member 63 is fixed with the V-shaped strip 2211, respectively. The other portion 23b of the resetting member 23 is also resisted against the V-shaped strip 2211. The second extension rod 22 is pulled by the connecting member 63 to compress the resetting member 23 to draw back downwardly, and the second extension rod 22 is stretched upwardly when the resetting member 23 is reset.

Furthermore, an inserting hook 224 is connected with the second post 221 for elastically clamping the UV sterilization member 30 to fix the second extension rod 22 with the UV sterilization member 30.

Figure 12:
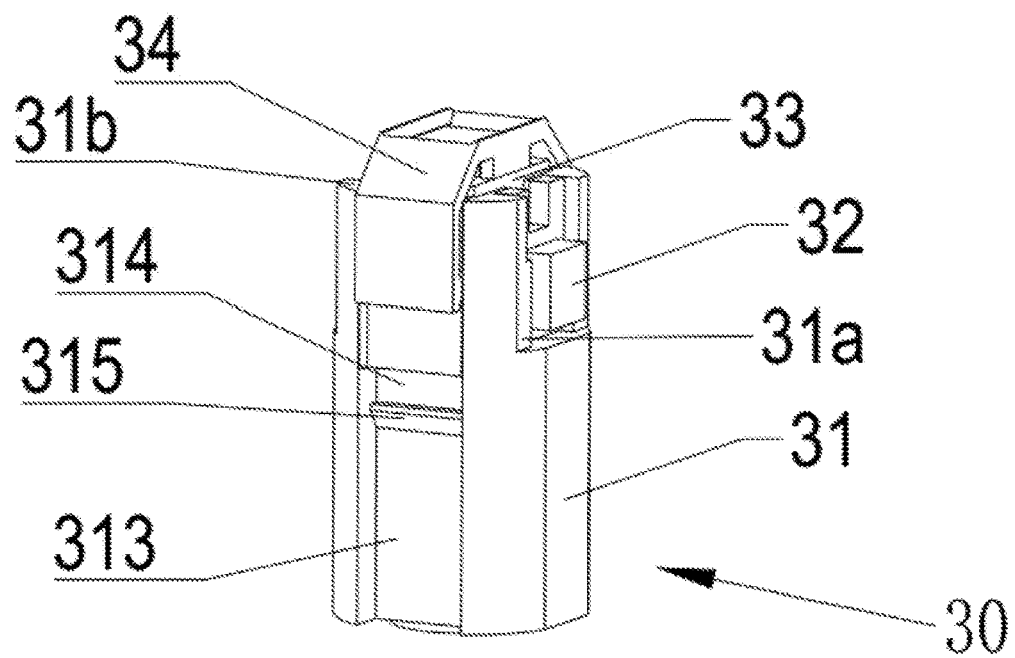
FIG. 12 is a schematic view of a UV sterilization member of the UV sterilization device of FIG. 1.
Figure 13:
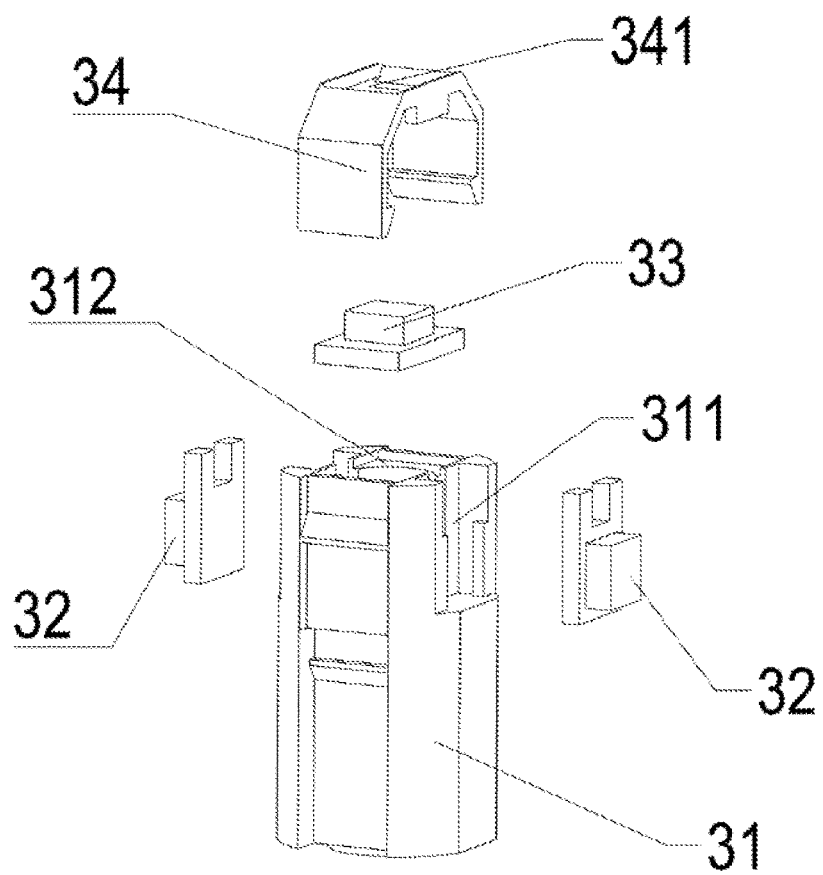
FIG. 13 is an exploded, schematic view of the UV sterilization member of the UV sterilization device of FIG. 1.

Referring to FIG. 1, FIG. 12 and FIG. 13, the UV sterilization member 30 includes a heat sink 31 elastically clamped with the inserting hook 224, a lateral LED 32 fixed with the outer side 31a of the heat sink 31, an end LED 33 fixed with the top portion 31b of the heat sink 31, and a pressing buckle 34 clamped on the end LED 33 and fixed with the heat sink 31.

Preferably, the pressing buckle 34 includes a window 341 through which the sterilization state of the container 500 can be observed by the end LED 33.

In an exemplary embodiment of the present disclosure, the lateral LED 32 and the end LED 33 respectively include ultraviolet LED light and blue LED light. The UV LED light has a wavelength of UVC band in the range of 150~300 nm, and the blue LED light has a wavelength of 400~470 nm.

In other exemplary embodiments of the present disclosure, the amount of the lateral LED 32 and the end LED 33 of the UV sterilization member 30 can be installed according to an actual demand so as to meet all-round disinfection requirement of the container 500, thereby the sterilization efficiency can be improved.

Preferably, the heat sink 31 includes a first mounting slot 311 for receiving the lateral LED 32 therein, and a second mounting slot 312 for receiving the end LED 33 therein.

Furthermore, the heat sink 31 further includes a sliding recess 313, a buckle 314 and a rail 315 formed between the sliding recess 313 and the buckle 314. The inserting hook 224 includes a base portion 2241 received in the sliding recess 323, and a hooking portion 2242 received in the buckle 314 and snapped with the rail 315.

In an exemplary embodiment of the present disclosure, the container 500 and the UV sterilization member 30 can rotate relative to each other. In other exemplary embodiments of the present disclosure, the container 500 can be stationary and the UV sterilization member 30 can rotate, or the container 500 can rotate and the UV sterilization member 30 can be stationary. It can be understood that both the container 500 and the UV sterilization member 30 can also be stationary for static sterilization.

During using the UV sterilization device 100, the motor 41 is driven to rotate along a first direction so that the rotating gear 51 and the single-groove pulley 521 are also driven to rotate along the first direction. And then, the driven gear 13 is also rotated to drive the container 500 to rotate with the rotating gear 51. At the same time, the connecting member 63 is wound on the single-groove pulley 521 along the first direction so that the pair of extension members 20 is compressed by pulling of the connecting member 63. When the pair of extension members 20 is compressed to its lowest compression position, the motor 41 is driven to rotate along a second direction opposite to the first direction, the pair of extension members 20 is stretched out along the second direction so as to achieve all-round sterilization of the container 500.

Although the features and elements of the present disclosure are described as embodiments in particular combinations, each feature or element can be used alone or in other various combinations within the principles of the present disclosure to the full extent indicated by the broad general meaning of the terms in which the appended claims are expressed.

What is claimed is:

1. A UV sterilization device for a container comprising:
a housing;
a base connected to the housing;
a receiving room formed between the housing and the base for receiving the container therein;
a pair of transmission members received in the receiving room and symmetrically mounted on the base to rotate relative to the base, each of the pair of transmission members comprising a clamp clamping with the container;
a pair of extension members received in the receiving room and symmetrically mounted on the base and passing through corresponding transmission members and then extending into the container so that the pair of extension members can stretch out and draw back relative to the container along an axial direction thereof;
a pair of UV sterilization members received in the receiving room, each UV sterilization member mounted on a corresponding extension member to move together with the corresponding extension member;
a driving member received in the receiving room and fixed with the base, the driving member comprising a motor received therein; and wherein
the motor is fixed with both the pair of transmission members and the pair of extension members, and configured to not only drive the pair of transmission members to rotate and then drive the container to rotate, but also drive the pair of extension members to stretch out and draw back relative to the container along the axial direction of the extension member to further drive a corresponding UV sterilization member to sterilize the container; and wherein
the transmission member further comprises a driven gear connected to the motor, and a connecting portion fixed with the clamp and the driven gear, and the motor is configured to drive the driven gear to rotate and then drive the container clamped by the clamp to rotate with the driven gear; and wherein
the UV sterilization device further comprises a rotating member received in the receiving room and comprising a rotating gear fixed with the motor and engaged with the driven gear, and a winding member which comprises a single-groove pulley fixed with the rotating gear and a connecting member, two opposite ends of the connecting member respectively connected to the pair of extension members for pulling the pair of extension members to stretch out and draw back along the axial direction of the extension member relative to the container, the motor configured to drive the rotating gear and the single-groove pulley to rotate so as to respectively drive the driven gear to rotate and the pair of extension members to coaxially stretch out and draw back.

2. The UV sterilization device as claimed in claim 1, wherein the clamp comprises a first clamping portion with a cone inner torus thereon, a second clamping portion coaxially arranged with the first clamping portion and an annular groove surrounded between the first clamping portion and the second clamping portion for receiving an opening of the container therein, and the diameter of the first clamping portion is greater than that of the second clamping portion.

3. The UV sterilization device as claimed in claim 1, wherein the single-groove pulley comprises an inner disk body, a connecting post fixedly connected with the rotating gear, and an outer disk body with a clamping slot extending along its radial direction from the outer disk body to an inner end surface of the inner disk body, the connecting member laterally passing through the clamping slot, all the inner disk body, the connecting post and the outer disk body coaxially arranged with the rotating gear, and the diameter of the outer disk body same as the diameter of the inner disk body, but greater than that of the connecting post.

4. The UV sterilization device as claimed in claim 3, wherein the base comprises a body, an upper plate mounted on the upper end of the body, and a baseboard mounted on the bottom end of the body, the upper plate comprising a pair of through-holes for the pair of transmission members correspondingly passing therethrough and a receiving recess with its opening facing downward for receiving the motor therein.

5. The UV sterilization device as claimed in claim 4, wherein the base further comprises an installing frame comprising a first fixing frame fixed with the upper plate, and a second fixing frame fixed with the first fixing frame.

6. The UV sterilization device as claimed in claim 5, wherein the first fixing frame comprises an installing hole connected with the through-hole, an installing portion and a hole, the transmission member passing through the through-hole to rotatably mount on the installing hole, and the motor comprises a motor body received in the receiving recess and mounted on the installing portion, and a motor shaft passing through the hole and fixed with the rotating gear.

7. The UV sterilization device as claimed in claim 6, wherein the second fixing frame comprises a fixing post passing through the installing hole and the through-hole, and a locating hole for the single-groove pulley passing therethrough, the pair of extension members respectively received in corresponding fixing posts so as to stretch out and draw back from the corresponding fixing post.

8. The UV sterilization device as claimed in claim 7, wherein the UV sterilization device further comprises a pulley assembly received in the receiving room and comprising a pulley frame fixed with the bottom of the fixing post, and a pair of pulleys rotatably mounted on the pulley frame, one of the two opposite ends of the connecting member fixed with one of the pair of extension members, the other of the two opposite ends of the connecting member passing through one of the pair of pulleys, the clamping slot and the other of the pair of pulleys in turn, and then fixed with the other of the pair of extension members.

9. The UV sterilization device as claimed in claim 8, wherein the extension member comprises a first extension rod received in the fixing post and configured to stretch out and draw back from the fixing post, a second extension rod and a resetting member respectively connected to the first extension rod, the second extension rod received in the first extension rod and configured to stretch out and draw back from the first extension rod, one portion of the resetting member fixed with the second extension rod and the opposite portion passing through both the first extension rod and the fixing post and then resisted against the pulley frame.

10. The UV sterilization device as claimed in claim 9, wherein the first and second extension rods and the fixing post are cooperatively connected to form a passageway for receiving the resetting member therein, and the connecting member is partially received in the passageway.

11. The UV sterilization device as claimed in claim 9, wherein the first extension rod comprises:
   a first hollow post comprising a pair of first L-shaped ribs coaxially arranged on its outer wall thereof, and a first ring protruding outward from its lower portion thereof and comprising a first gap formed thereon;
   the fixing post comprising a second barrier formed on its inner wall thereof, and a second blocking torus connected to the upper portion of the second barrier and comprising a second notch formed thereon;
   the second barrier passing through both the first gap and the first L-shaped rib to slide in the second notch; and wherein the first ring is resisted against the second blocking torus when the first L-shaped rib slides to the top of the fixing post.

12. The UV sterilization device as claimed in claim 11, wherein the first post comprises a first barrier formed on its inner sidewall thereof, and a first blocking torus connected to the upper end of the first barrier and comprising a first notch formed thereon;
   the second extension rod comprising a second hollow post comprising a pair of second L-shaped ribs coaxially arranged on its outer sidewall thereof, and a second ring protruding outward from its lower end thereof and comprising a second gap formed thereon;
   the first barrier passing through both the second gap and the second L-shaped rib to slide in the first notch; and wherein the second ring is resisted against the first blocking torus when the second L-shaped rib slides to the top of the first extension rod.

13. The UV sterilization device as claimed in claim 12, wherein the second post further comprises a V-shaped strip, the two opposite ends of the connecting member fixed with the V-shaped strip, respectively, and the other portion of the resetting member also resisted against the V-shaped strip.

14. The UV sterilization device as claimed in claim 12, wherein an inserting hook is connected with the second post for elastically clamping the UV sterilization member to fix the second extension rod with the UV sterilization member.

15. The UV sterilization device as claimed in claim 14, wherein the UV sterilization member comprises a heat sink elastically clamped on the inserting hook, a lateral LED fixed with the outer side of the heat sink, an end LED-fixed with the top portion of the heat sink, and a pressing buckle clamping the end LED and fixed with the heat sink.

16. The UV sterilization device as claimed in claim 15, wherein the heat sink comprises a first mounting slot for receiving the lateral LED therein, and a second mounting slot for receiving the end LED therein.

17. The UV sterilization device as claimed in claim 16, wherein the heat sink further comprises a sliding recess, a buckle and a rail formed between the sliding recess and the buckle, and the inserting hook comprises a base portion received in the sliding recess, and a hooking portion received in the buckle and snapped with the rail.

* * * * *